United States Patent [19]

Lowder

[11] Patent Number: 4,738,621
[45] Date of Patent: Apr. 19, 1988

[54] HAND HELD DENTAL INSTRUMENT FOR CUTTING INTERPROXIMAL SPACES

[75] Inventor: James T. Lowder, Columbus, Ohio

[73] Assignee: Abrasive Technology, Inc., Westerville, Ohio

[21] Appl. No.: 893,229

[22] Filed: Aug. 5, 1986

[51] Int. Cl.$^4$ ............................................. A61C 3/06
[52] U.S. Cl. ..................................... 433/142; 433/147
[58] Field of Search ............... 433/141, 142, 144, 146, 433/153, 166, 165, 147; 51/205 R, 211 R

[56] References Cited

U.S. PATENT DOCUMENTS

| | | | |
|---|---|---|---|
| 409,837 | 8/1889 | Hardie | 433/166 |
| 2,087,023 | 7/1937 | Decker | 51/211 R |
| 4,483,676 | 11/1984 | Thierman | 433/142 |

Primary Examiner—John J. Wilson
Assistant Examiner—Adriene J. Lepiane
Attorney, Agent, or Firm—Francis T. Kremblas, Jr.

[57] ABSTRACT

A hand held abrasive dental instrument for use in cutting the proximal aspect of a tooth's surface to create an interproximal space between abutting tooth surfaces. The instrument features a thin circular disc shaped abrasive cutting member provided with a coating of abrasive material over one of the circular surfaces of the disc which is rotatably mounted between abutting handle portions. The handle portions serve to provide means for convenient grasping of the instrument by the user in a manner which permits facile manipulation of the cutting disc between abutting teeth. The handle portions are constructed to automatically lock the disc against rotation when grasped in the normal operational mode so that effective cutting can be accomplished. However, upon releasing the grasping pressure, the disc may be rotated to position an unused portion of the abrasive coating for operative use.

5 Claims, 1 Drawing Sheet

HAND HELD DENTAL INSTRUMENT FOR CUTTING INTERPROXIMAL SPACES

BACKGROUND

The increased popularity and usage of composite restorative materials in dentistry have generated the need for ever increasing sophistication in the finishing of these materials. Some of these materials, which consist of a hard glassy or mineral filler in a resinous bonding system, were discovered to be harder and more abrasive than many of the abrasive materials traditionally employed by the dental profession. Thus diamond abrasives have become very popular for shaping, finishing and polishing composite restorative materials. Some of the recent advances in this field have been the successful usage of ultra-fine, micron sized diamond instruments.

One problem which had presisted until the present invention was the satisfactory finishing in interproximal locations (abutting tooth surfaces). Composite restorations in interproximal areas frequently resulted in inadequate space to position any instrument for finishing. At times, there was no space at all, as the composite material bridged and bonded from one tooth to the adjacent one, conventional rotary instruments may be effectively used after a sufficient interproximal space is present to contour and finish proximal tooth surfaces, however, they are generally less than satisfactory to create the necessary space initially.

Therefore there was a need for a low cost instrument of this type which could be economically manufactured and assembled and which was efficient on a cost per usage basis to the user.

SUMMARY OF THE INVENTION

The present invention relates generally to dental instruments and particularly to a hand held abrasive cutting instrument which may be effectively and safely manipulated within the interproximal areas between abutting teeth to open this space for proper finishing of composite restorative techniques.

In accordance with the present invention an abrasive coated disc shaped diamond instrument is mounted between two abutting handle portions in a releasably fixed manner. The disc is fixed against rotation when the handle is grasped in the normal manner for use of the cutting disc. However, upon releasing the grasping pressure applied to the handle portion in a parallel direction to the axis of the disc, it may be manually rotated to expose a fresh abrasive surface in the optimum position relative to the handle for manipulation as required.

As another aspect of the present invention, the handle portion consists of two similarly configured plates which are fitted to one another in a simple assembly step. One side plate includes integrally formed pins which mate with holes provided in the other plate in an interference fit when the two plates are aligned and pressed together.

One of these pins also serves to rotatably receive the cutting disc between the two handle portions with at least approximately an 180 degree arc of the disc extending outwardly from the handle. The opposing inner surfaces of the handle in the area of the disc are provided with a slight relief to create sufficient clearance for the disc to be rotated on its pin unless grasping pressure filling the interproximal area entirely. The only means for opening this space were small diameter diamond rotary instruments. The results were not always satisfactory, the procedure being very tedious and highly dependent on individual skill. Usually, the resultant interproximal space was greater than desired.

Prior to the present invention a dental instrument which could be safely used to conservatively restore the interproximal space was developed which consisted of a thin diamond coated disc which was immovably fixed between two handle portions which the dentist could grasp for manual manipulation of the disc. While this device proved to be a desirable configuration to perform the required task, it's manufacture was relatively difficult and time consuming. Further the abrasive coating on the whole of the disc's surface was not capable of use in an efficient manner, which in combination with the cost of manufacture, detracted greatly from the utility and desirability of the instrument.

Abrasive coated elongated strips or very small is applied to the side portions parallel to the axis of the disc. Upon application of the normal grasping pressure in this manner, these inner surfaces engage the disc and prevent rotation thereof during use of the intended cutting procedure.

IN THE DRAWINGS

DETAILED DESCRIPTION

Figures 1, 2:
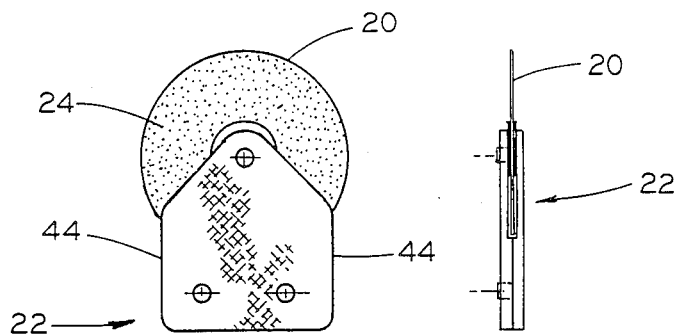
FIG. 1 is a front elevational view of a hand-held dental instrument constructed in accordance with the present invention.
FIG. 2 is a side elevational view of the instrument shown in FIG. 1.
Figure 3:
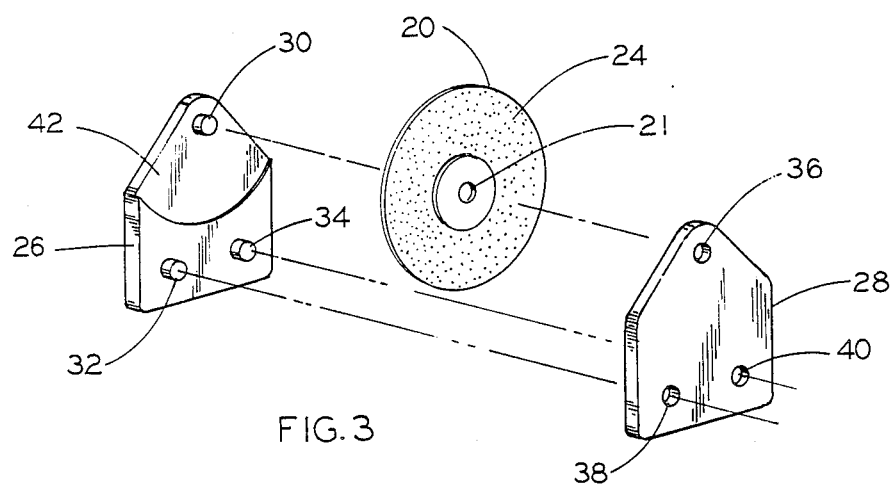
FIG. 3 is a perspective view of the instrument shown in FIG. 1 illustrating the components in exploded relationship.

A hand-held dental instrument for cutting within the interproximal spaces between human teeth constructed in accordance with the present invention is shown in FIG. 1.

The instrument includes a thin circular disc 20 which is mounted to a handle portion indicated generally at 22. Disc 20 is provided with a hole 21 in the center thereof.

Preferably, only one face 24 of disc 22 is provided with a coating of abrasive material, such as very fine diamond grit. The other face, being free of abrasive, permits the disc to be safely used for conservative cutting procedures on the proximal surface of a tooth without inadvertently cutting the surface of an abutting tooth.

The abrasive coating may be bonded to the disc in a conventional well-known manner, such as electroplating, for example.

Handle 22 comprises a pair of similarly shaped side plate 26 and 28 mounted together in a face to face relationship. Preferably, side plates 26 and 28 comprise a molded plastic material, such as an acrylic for example, and are configured to be conveniently grasped between the thumb and forefinger of the user.

Side plate 26 is provided with three integrally formed pins 30, 32 and 34 which extend outwardly from the face of the plate. Side plate 28 is provided with three holes 36, 38 and 40 which are aligned to mate with pins 30, 32 and 34 when the plates 26 and 28 are aligned with one another with the pins disposed in a respective hole.

The lower holes 36 and 38 are preferably conformed to receive a respective one of pins 32 and 34 in an interference fit to firmly hold the plates together in a releasably locked manner.

Disc 20 is rotatably mounted on pin 30 which, upon assembly, extends through center hole 21 of disc 20 and into hole 36 of side plate 28. The face of plate 26, carrying the pins 30, 32 and 34, is preferably provided with an arcuate shaped relief area 42 coextensive with the portion of disc 20 disposed between plates 26 and 28 to provide a small clearance accomodating the thickness of disc 20 to permit rotation of disc 20 relative to handle 22. Further, hole 36, preferably is conformed to more freely accept pin 30 relative to the interference fit between pins 32 and 34 and the respective holes 38 and 40.

The plastic side plates 26 and 28 are movable toward one another to the extent that normal grasping pressure between the thumb and forefinger, when holding the instrument for its intended use, functions to reduce the clearance provided by relief area 42 and to cause sufficient engagement between disc 20 and the inward faces of plates 26 and 28 to prevent rotation of disc 20 relative to handle 22. It is important that disc 20 be fixed against rotation when in use to assure effective and efficient cutting action.

However, as the abrasive coating upon disc 20 becomes worn, the user may easily rotate disc 20 relative to handle 22 sufficiently to expose a fresh abrasive area to a working position. Disc 20 may be easily rotated on pin 30 when the grasping pressure is released upon plates 26 and 28 parallel to the axis of pin 30 and disc 20. This may be accomplished by holding handle 22 on opposing edges 44 with the fingers of one hand while using the fingers of the other hand to rotate disc 20.

Figure 4:
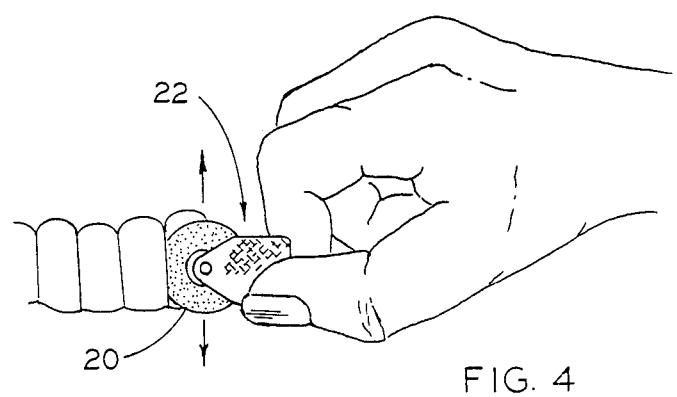
FIG. 4 is a perspective view illustrative of the use of the instrument shown in the preceding Figures.

The cutting disc 20 is primarily designed for use in opening up close proximal contact areas between teeth, such as illustrated in FIG. 4. Such a hand-held instrument provides maximum control for conservative cutting action required in tooth restorative procedures, or for placement of rubber dams and dental floss. For such purposes, the disc is very thin, preferably 0.10 to 0.20 mm.

With very tight interproximal spaces caused by excess restorative composite materials used in such procedures or those which are naturally occurring, this instrument is convenient for use in creating or restoring sufficient spacing to perform further cutting and shaping with other instruments or to remove the excess material which has been deposited during tooth restorative techniques.

In use, the dentist user may begin the cutting action from the anterior or posterior side of the tooth by inserting the extreme edge of disc 20 against the surface to be cut. The handle 22 provides convenient control and added reach for manipulation of the disc's surface in a reciprocating manner. Typically, a rotary manipulation may be combined therewith by the coordinated movement of the thumb and forefinger grasping the handle 22.

In accordance with the present invention, even the lightest of usual gripping pressure applied in grasping handle 22, as seen in FIG. 4, is sufficient to prevent disc 20 from rotating upon pin 30 as the inner surfaces of plates 26 and 28 are caused to engage the surface of disc 20 disposed therebetween. When disc 20 is used for the intended cutting action described, rotation of the disc would tend to degrade the cutting effects desired.

As the abrasive coating begins to wear upon the surface being used, the user merely rotates the disc as described above to expose fresh abrasive and continues the cutting procedure. In this manner, the whole surface area of the coated face of disc 20 may be employed.

It has been found that the prior disc cutting instrument wherein the disc was fixed in a handle portion was significantly less efficient relative to the use of the abrasive coated area. In order to effectively manipulate the disc for work within the interproximal spaces, the user held the handle in a manner which used only about 30 to 35 percent of the exposed surface area of the disc. However, by providing the selective rotation of the disc as described herein, any portion of the disc surface may be aligned as desired by the user. This permits the user to grasp the handle 22 in the same manner and attitude and yet use the whole abrasive surface area of the disc effectively. This represents a 300 to 400 percent improvement in the efficient use of the expensive diamond abrasive and provides greater convenience to the user.

The construction of the dental instrument also lends itself to inexpensive manufacture and assembly. The side plates 26 and 28 may be injection molded components. The complete instrument is easily and quickly assembled by merely inserting pin 30 through hole 21 of disc 20 and then aligning holes 36, 38 and 40 with the respective pins 30, 32 and 34. Pressing the aligned plates together forces the pins into a respective hole.

What is claimed is:

1. A manually manipulated abrasive cutting instrument grasped between the thumb and forefinger by the user for cutting within the proximal space between adjacent tooth surfaces, comprising, a circular disc-shaped cutting member provided with a coating of abrasive particles on the surface area of one side thereof and rotatably mounted between two generally planar side plates forming a handle portion with a substantial portion of the surface area of said disc extending outwardly from said plates, said plates aligned in parallel face to face close-fitting relationship and resiliently movable toward and away from one another in the area coextensive with the portion of said disc mounted between said plates to define a first position with said plates free of force-transmitting engagement with said disc permitting said disc to be angularly rotated relative to said handle portion and a second position defined when said plates are forced inwardly toward one another into frictional engagement with said disc to prevent rotation of said disc during manipulation of said disc for cutting of said tooth surfaces.

2. The dental instrument defined in claim 1 wherein one of the faces of side plates is provided with a plurality of integrally formed outwardly extending pins spaced from one another; and the face of said other side plate includes a plurality of holes configured to receive said pins in an interfering fit relationship; said circular disc being rotatably mounted on one of said pins.

3. The dental instrument defined in claim 2 wherein said disc has a thickness between 0.10 and 0.20 millimeters.

4. A manually manipulated abrasive dental instrument for the cutting of the proximal aspect between abutting tooth surfaces comprising, in combination, a handle portion conformed to be grasped between the thumb and forefinger, said handle portion including a first side plate provided with at least three integrally formed outwardly extending pins spaced from one another to define a triangular configuration between said pins and a second side plate mounted in closely spaced face to face relationship with said first side plate and provided with at least three openings receiving said pins in an interference fit relationship; a circular disc-shaped cutting member provided with opposing planar surfaces disposed between said side plates and rotatably mounted on one of said pins for selective angular positioning of said planar surfaces relative to said handle, said cutting member having at least approximately one-half of the surface of said disc extending outwardly from said side plates, at least one of said planar surfaces of said disc being coated with abrasive particles; and said side plates being resiliently movable toward one another for frictional engagement with the surfaces of said disc upon application of grasping pressure on said side plates in a direction parallel to the axis of said disc to fix said disc in a given angular position relative to said handle portion.

5. A manually manipulated interproximal abrasive cutting instrument grasped between the thumb and forefinger by the user for cutting within the proximal space between adjacent tooth surfaces, comprising, a circular disc-shaped cutting member provided with a coating of abrasive particles on the surface area of at least one side thereof and rotatably mounted between two generally planar side plates forming a handle portion with a substantial portion of the surface area of said disc extending outwardly from said plates, said plates aligned in parallel face to face relationship and movably connected to one another between a working position and a non-working position, said working position being defined when said plates are urged toward one another into force engaging relationship with said disc to prevent angular rotation of said disc and said non-working position being defined when said plates are in a non-force engaging relationship with said disc permitting angular rotation thereof.

* * * * *